United States Patent [19]
Mathies et al.

[11] Patent Number: 5,274,240
[45] Date of Patent: * Dec. 28, 1993

[54] CAPILLARY ARRAY CONFOCAL FLUORESCENCE SCANNER AND METHOD

[75] Inventors: Richard A. Mathies, Contra Costa County; Xiaohua C. Huang, Santa Clara County; Mark A. Quesada, San Francisco County, all of Calif.

[73] Assignee: The Regents of the University of California, Oakland, Calif.

[*] Notice: The portion of the term of this patent subsequent to Feb. 25, 2009 has been disclaimed.

[21] Appl. No.: 840,501

[22] Filed: Feb. 24, 1992

Related U.S. Application Data

[63] Continuation-in-part of Ser. No. 531,900, Jun. 1, 1990, Pat. No. 5,091,652, and a continuation-in-part of Ser. No. 463,757, Jan. 12, 1990, abandoned.

[51] Int. Cl.⁵ .................................... G01N 21/64
[52] U.S. Cl. .................. 250/458.1; 250/459.1; 250/461.1
[58] Field of Search ............... 250/458.1, 459.1, 461.1, 250/461.2; 356/344; 204/180.1, 182.1, 299 R, 182.8

[56] References Cited

U.S. PATENT DOCUMENTS

| | | | |
|---|---|---|---|
| 4,162,405 | 7/1979 | Chance et al. | 250/461 |
| 4,354,114 | 10/1982 | Karnaukhov et al. | 250/458.1 |
| 4,572,671 | 2/1986 | Kaneko | 356/444 |
| 4,580,059 | 4/1986 | Wolfbeis et al. | 250/459.1 |
| 4,734,578 | 3/1988 | Horikawa | 250/234 |
| 4,781,464 | 11/1988 | Allington et al. | 356/419 |
| 4,791,310 | 12/1988 | Honig et al. | 250/458.1 |
| 4,811,218 | 3/1989 | Hunkapiller et al. | 364/413.01 |
| 4,833,332 | 5/1989 | Robertson, Jr. et al. | 250/458.1 |
| 4,855,225 | 8/1989 | Fung et al. | 435/6 |
| 4,893,008 | 1/1990 | Horikawa | 250/234 |
| 5,006,210 | 4/1991 | Yueng et al. | 204/180.1 |
| 5,091,652 | 2/1992 | Mathies et al. | 250/458.1 |
| 5,108,179 | 4/1992 | Myers | 356/344 |

FOREIGN PATENT DOCUMENTS

| | | |
|---|---|---|
| 0157280 | 3/1985 | European Pat. Off. . |
| 0214713 | 5/1986 | European Pat. Off. . |
| 2155176 | 1/1985 | United Kingdom . |
| 2180941 | 6/1986 | United Kingdom . |
| 405480 | 1/1991 | United Kingdom ............. 250/461.2 |

OTHER PUBLICATIONS

Luckey et al., 'High Speed DNA Sequencing by Capillary Electrophoresis', Nucleic Acids Research, vol. 18, No. 15, 1990, pp. 4417-4421.

Zagursky et al., 'DNA Sequencing Separations in Capillary Gels on a Modified Commercial DNA Sequencing Instrument', Bio Techniques, vol. 9, No. 1, 1990, pp. 74-79.

Mathies et al., 'High-sensitivity Single-Molecule Fluorescence Detection; Bioimaging and Two-Dimensional Spectroscopy, SPIE vol. 1205, 1990, pp. 52-59.

Jorgenson, J. W.; Lukacs, K. D.; *Capillary Zone Electrophoresis*, Science 1983, 222, 266-272.

(List continued on next page.)

Primary Examiner—Constantine Hannaher
Assistant Examiner—Edward J. Glick
Attorney, Agent, or Firm—Flehr, Hohbach, Test, Albritton & Herbert

[57] ABSTRACT

A laser-excited capillary array scanner including a plurality of capillaries having a parallel, side-by-side, coplanar relationship and a laser-excited confocal fluorescence detector for detecting fluorescence from selected interior volumes of each of the capillaries sequentially and repetitively during electrophoresis or other separation method. The invention also relates to a method of analyzing a plurality of capillaries, with a single scanner, by scanning a plurality of capillary passages in side-by-side relationship, and periodically and repetitively detecting fluorescence from each capillary passage during electrophoresis or other separation method.

28 Claims, 11 Drawing Sheets

OTHER PUBLICATIONS

Gordon, M. J. Huang, X.; Pentoney, S. L., Jr.; Zare, R. N.; *Capillary Electrophoresis*, Science 1988, 242, 224–228.

Ewing, A. G.; Wallingford, R. A.; Olefirowicz, T. M.; *Capillary Electrophoresis*, Anal. Chem. 1989, 61, 292A–303A.

Karger, B. L.; Cohen, A. S.; Guttman, A.; *High-Performance Capillary Electrophoresis in the Biological Sciences*, J. Chromatogr. 1989, 492, 585–614.

Kuhr, W. G.; *Capillary Electrophoresis*, Anal. Chem. 1990, 62, 405R–414R.

Cohen, A. S.; Najarian, D. R.; Paulus, A.; Guttman, A.; Smith, J. A.; Karger, B. L.; *Rapid separation and purification of oligonucleotides by high-performance capillary gel electrophoresis*, Proc. Natl. Acad. Sci, 1988, 85, 9660–96633.

Heiger, D. N.; Cohen, A. S.; Karger, B. L.; *Separation of DNA restriction fragments by high performance capillary electrophoresis with low and zero crosslinked polyacrylamide using continuous and pulsed electric fields*, J. Chromatogr. 1990, 516, 33–48.

Swerdlow, H.; Wu, S.; Harke, H.; Dovichi, N. J.; *Capillary gel electrophoresis for DNA sequencing; Laser-induced fluorescence detection with the sheath flow cuvette*, J. Chromatogr. 1990, 516, 61–67.

Swerdlow, H.; Gesteland, R.; *Capillary gel electrophoresis for rapid, high resolution DNA sequencing*, Nucleic Acids Res. 1990, 18, 1415–1419.

Drossman, H.; Luckey, J. A.; Kostichka, A. J.; D'Cunha, J.; Smith, L.M.; *High-Speed Separations of DNA Sequencing Reactions by Capillary Electrophoresis*, Anal Chem. 1990, 62, 900–903.

Compton, S. W.; Brownlee, R. G.; *Capillary Electrophoresis*, Bio Techniques 1988, 6, 432–439.

Cohen, A. S.; Najarian, D.; Smith, J. A.; Karger, B. L.; *Rapid Separation of DNA Restriction Fragements using Capillary Electrophoresis*, J. Chromatogr. 1988, 458, 323–333.

Cheng, Y. F.; Dovichi, N. J.; *Subattomole Amino Acid Analysis by Capillary Zone Electrophoresis and Laser-Induced Fluorescence*, Science 1988, 242 562–564.

Hjerten, S.; Elenbring, K.; Kilar, F.; Liao, J. L.; Chen, A. J. C.; Sieberg, C.J.; Zhu, M.D.; *Carrier-Free Zone Electrophoresis, Displacement Electrophoresis and Isoelectric Focusing in a High-Performance Electrophorsis Apparatus*, J. Chromatogr. 1987, 403, 47–61.

Gassmann, E.; Kuo, J. E.; Zare, R. N.; *Electrokinetic Separation of Chiral Compounds*, Science 1985, 230, 813–814.

Ansorge, W.; Sproat, B.; Stegemann, J.; Schwager, C.; Zenke, M.; *Automated DNA sequencing: ultrasensitive detection of fluorescent bands during electrophoresis*, Nucleic Acids Res. 1987, 15, 4593–4602.

Brumbaugh, J. A.; Middendorf, L. R.; Grone, D. L.; Ruth, J. L.; *Continuous on-line DNA sequencing using oligodeoxynucleotide primers with multiple fluorophores*, Proc. Natl. Acad Sci. USA 1988, 85, 5610–5614.

Smith, L. M.; Sanders, J. Z.; Kaiser, R. J.; Hughes, P.; Dodd, C.; Connell, C. R.; Heiner, C.; Kent, S. B. H.; Hood, L. E.; *Fluorescence detection in automated DNA sequence analysis*, Nature 1986, 321, 674–679.

Prober, J. M.; Trainor, G. L.; Dam, R. J.; Hobbs, F. W.; Robertson, C. W.; Zagursky, R. J.; Cocuzza, A. J.; Jensen, M. A.; Baumeister, K.; *A System for Rapid DNA Sequencing with Fluorescent Chain-Terminating Dideozynucleotides*, Science 1987, 238, 336–341.

Glazer, A. N.; Peck, K.; Mathies, R. A.; *A stable double-stranded DNA-ethidium homodimer complex: Application to picogram fluorescence detection of DNA in agarose gels*, Proc. Natl. Acad. Sci. USA 1990, 87, 3851–3855.

Rye, H. S.; Quesada, M. A.; Peck, K.; Mathies, R. A.; Glazer, A. N.; *High-sensitivity two-color detection of double-stranded DNA with a confocal fluorescence gel scanner using ethidium homodimer and thiazole orange*, Nucleic Acids Res. 1991, 19, 327–333.

Quesada, M. A.; Rye. H. S.; Gingrich, J. C.; Glazer, A. N.; Mathies, R. A.; *High-Sensitivity DNA Detection with a Laser-Excited confocal Fluorescence Gel Scanner*, Bio Techniques 1991, 10 616–625.

Rye, H. S.; Yue, S.; Quesada, M. A.; Haugland, R. P.; Mathies, R. A.; Glazer, A.N.; *Picogram Detection of Stable Dye-DNA Intercalation Complexes with a Two-Color Laser-Excited Confocal Fluorescence Gel Scanner*, Paper submitted to Methods in Enzymology, RECOMBINANT DNA. Part H; R. Wu, ed.

L. Hernandez, R. Marquina, J. Escalona, N. A. Guzman, *Detection and quantification of capillary electrophoresis zones by fluorescence microscopy*, J. Chomatogr. 502, 247–255 (1990).

L. Hernandez, J. Escalona, N. Joshi, N. Guzman, *Laser-induced fluorescence and fluorescence microscopy for capillary electrophoresis zone detection*. J. Chromatogr. 559, 183–196.

Smith, L. M.; *High-speed DNA sequencing by capillary gel electrophoresis*, Nature 1991, 349, 812–813.

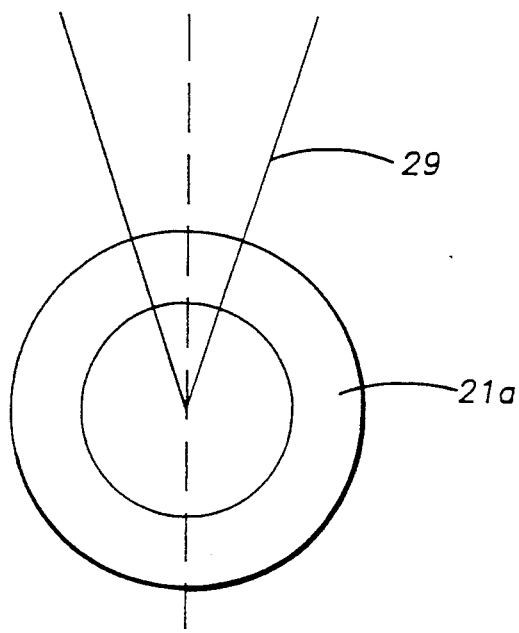
FIG.—4A
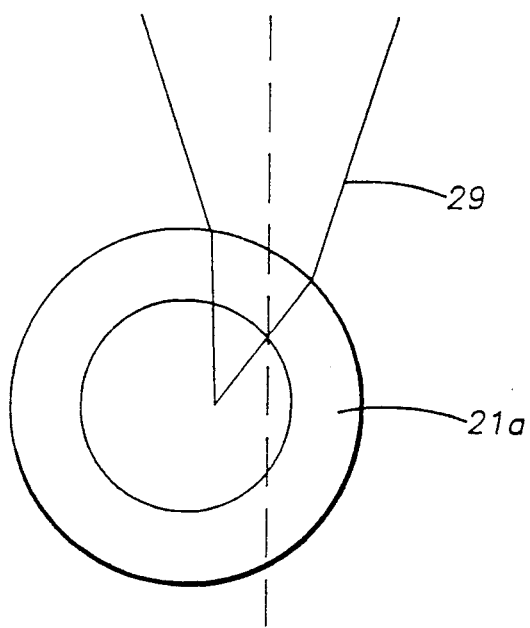
FIG.—4B

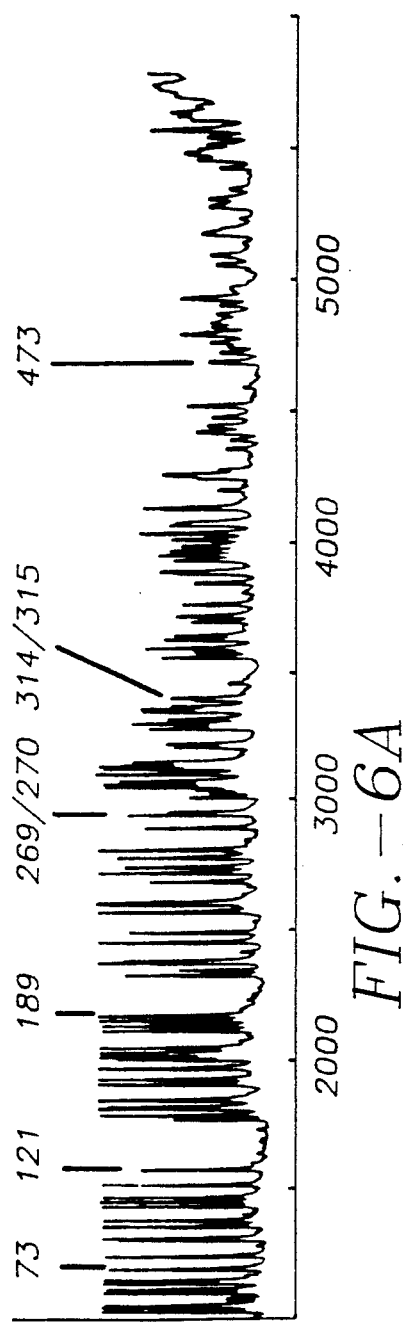
FIG.—6A
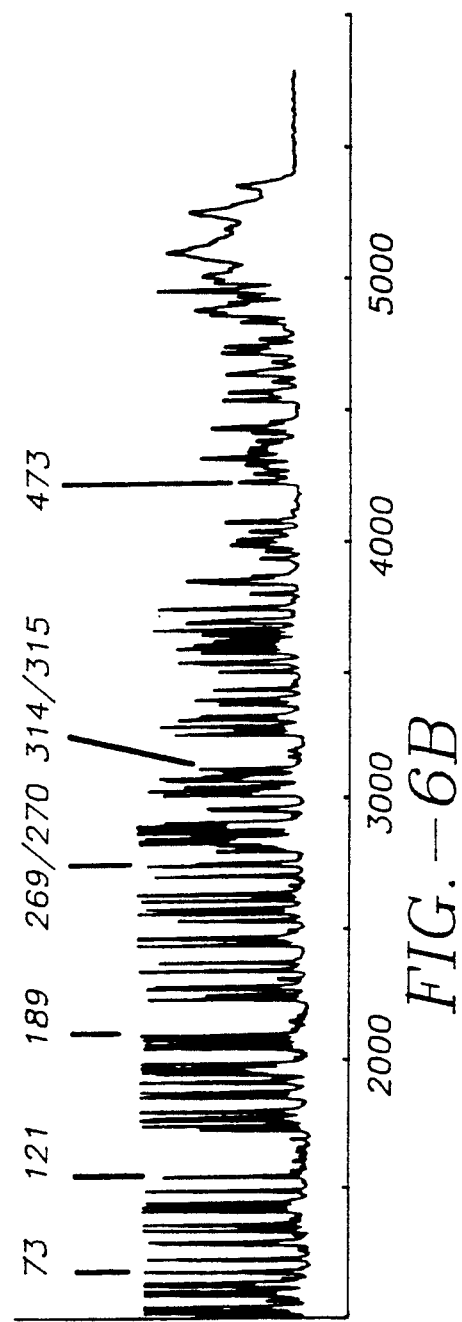
FIG.—6B

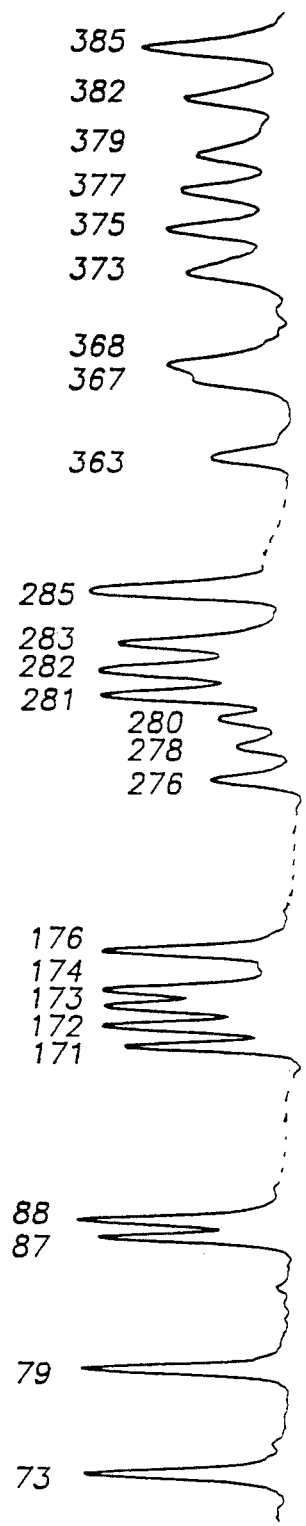
FIG.—7A
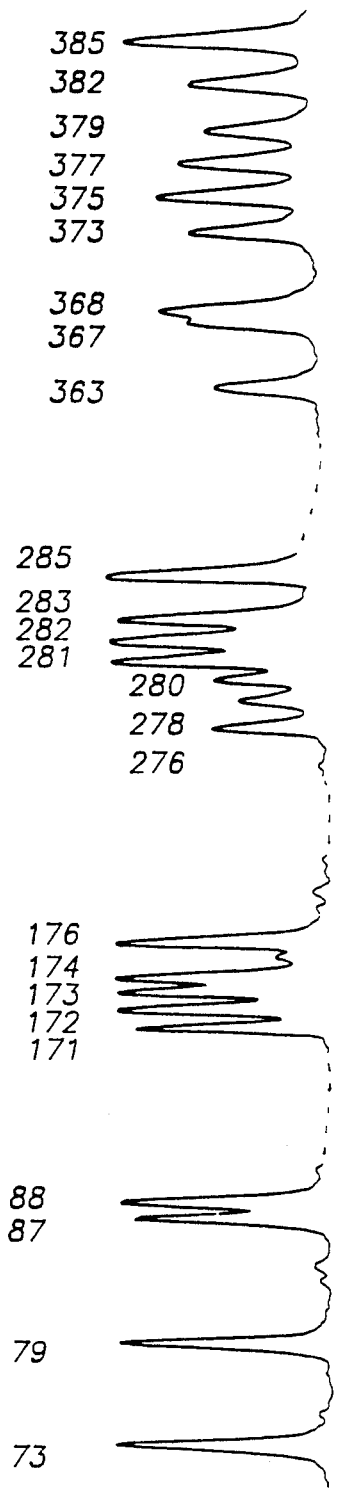
FIG.—7B

CAPILLARY ARRAY CONFOCAL FLUORESCENCE SCANNER AND METHOD

This invention was made with U.S. Government support under Grant Contract No. DIR-87-20382 awarded by the National Science Foundation, and Grant Nos. 88-ER-60706 and 91-ER-61125 awarded by the Department of Defense. The U.S. Government has certain rights in this invention.

RELATED APPLICATIONS

This application is a continuation-in-part of copending application Ser. No. 07/531,900 filed Jun. 1, 1990, entitled Laser Excited Confocal Microscope Fluorescence Scanner and Method, now U.S. Pat. No. 5,091,652; a continuation-in-part of Ser. No. 07/463,757 filed Jan. 12, 1990, now abandoned.

BRIEF DESCRIPTION OF THE INVENTION

This invention relates generally to a capillary array scanner and method, and more particularly, to a capillary array confocal fluorescence scanner and method for detecting electrophoretic, chromatographic or other separations performed on arrays of capillaries.

Capillary electrophoresis (CE) has found widespread application in analytical and biomedical research, and the scope and sophistication of CE is still rapidly advancing[1-5]. Gel-filled capillaries have been employed for the rapid separation and analysis of synthetic polynucleotides[6], DNA sequencing fragments[7-11] and DNA restriction fragments[12,13]. Open-tube capillary electrophoresis has attained subattomole detection levels in amino acid separations[14], and proven its utility for the separation of proteins, viruses and bacteria[15]. Separation of the optical isomers of dansyl amino acids has also been successfully demonstrated[16]. Micellar electrokinetic capillary chromatography, isoelectric focusing, and on-column derivation can all be performed in capillary columns, demonstrating the utility of capillaries as an analytical and micropreparative tool[4,5].

The advantages of CE arise intrinsically from the use of a small inside diameter (20–200 $\mu$m) capillary. High electric fields can be applied along small diameter fused-silica capillaries without a significant increase in the temperature of the separation medium or column. Since the electrophoretic velocity of the charged species is proportional to the applied field, CE can achieve rapid, high-resolution separation. The reduced Joule-heating in CE is a result of the very low current passing through the capillary, the large surface-to-volume ratio of the capillary channel, the use of thin capillary walls ($\sim 50$–150 $\mu$m), and the high thermal conductivity of the wall material[1].

Although CE provides rapid analysis, thus far the total throughout is not high because only one capillary can be analyzed at a time. Developing a method to increase the throughput of CE is a challenging and important task. One possible approach is to employ a much higher electric field which would provide faster separations. Higher electric fields, however, often introduce overheating of the columns and column failure.

Another way to increase the throughput is to run a large number of capillary separations in parallel. This approach uses an array of capillaries and is therefore called capillary array electrophoresis (CAE). CAE is potentially advantageous because the individual capillaries can be independently manipulated at the inlet, thereby facilitating rapid, parallel loading of multiple samples. In our approach, the capillaries are combined into a ribbon at the outlet for ease of parallel, on-column detection. In this way, a two order-of-magnitude increase in CE throughput should be achieved because hundreds of capillaries can be easily bundled for detection.

An important problem confronting capillary array electrophoresis is detection. Since small amounts of sample are injected in a capillary, a high-sensitivity detection system is indispensable. Laser-excited fluorescence has proven to be a sensitive detection method in capillary electrophoresis and in DNA sequencing[7-11, 14, 17-21]. In most laser-excited fluorescence detection schemes, the incident laser beam and the emitted fluorescence are perpendicular to each other. It is difficult to configure a system to detect an array of capillaries using this geometry. We have recently introduced a laser-excited, confocal-fluorescence gel scanner which provides enhanced detection of fluorescently labeled DNA in slab gels[22-26]. This detection system uses an epi-illumination format where the laser is focused on the sample by a microscope objective and the emitted fluorescence is gathered by the same objective using a 180° geometry followed by confocal detection. This geometry is ideal for on-column detection of capillaries. Using confocal excitation and detection, the depth of a field of the optical system is sufficiently small that only the interior of the capillary is probed. Background scattering, stray fluorescence and reflections from capillary wall are rejected by spatial and spectroscopic filters. Also, the high numerical aperture of the microscope objective gathers the fluorescence very efficiently and presents a high quality image to the pinhole spatial filter. The utility of fluorescence microscope detection for CE has been recognized in previous studies using static optical systems to detect single capillaries[27,28].

We show here that the ideal way to use a confocal fluorescence detector to detect an array of capillaries is to scan the capillary array past the detector. This format has several advantages that enhance the signal-to-noise ratio: (1) the entire cross-section of the electrophoresis band is sampled as it passes down the capillary and through the detection region; (2) problems due to photobleaching of the band that limit the sensitivity are minimized because the entire band is sampled and the optical system is constantly moving across the band being sampled; and (3) the cylindrical lens effect of the capillary walls permits extended detection of the separation channel that enhances the signal-to-noise ratio. These advantages mean that confocal scanning is a uniquely powerful way to perform high-sensitivity detections of separations on an array of capillary columns.

OBJECTS AND SUMMARY OF THE INVENTION

It is an object of this invention to provide a method and apparatus for increasing throughput in capillary separations.

It is another object of this invention to provide a method and apparatus for scanning an array of capillaries to detect separations of substances in the capillaries.

It is a further object of this invention to provide a high sensitivity fluorescence detection system for analyzing the interior of a number of parallel capillaries.

It is a further object of this invention to provide an apparatus and method for analyzing a number of separations in an array of capillaries which can be independently manipulated at their inlet to facilitate parallel loading and which are combined in a ribbon array for detection of the separations by a confocal scanner.

It is still a further object of this invention to provide a laser-excited confocal fluorescence detection system and method for analyzing during electrophoresis the gel in the interior of each capillary of a capillary ribbon comprising a plurality of capillaries disposed in side-by-side relationship.

It is still a further object of this invention to provide a laser-excited fluorescence capillary scanner for scanning an array of capillaries during CE.

It is a further object of this invention to provide a laser-excited fluorescence scanner which detects separations across the capillary channel to sample the entire separation band.

It is a further object of this invention to provide an apparatus and method for analyzing DNA sequencing in an array of capillaries which can be independently manipulated at their inlet to facilitate parallel loading and which are combined in a ribbon array for detection of the separations by a confocal scanner.

It is still a further object of this invention to provide a laser-excited confocal fluorescence detection system and method for analyzing during gel electrophoresis DNA fragments in each capillary of a capillary ribbon comprising a plurality of gel-filled capillaries disposed in side-by-side relationship.

It is a further object of this invention to provide a capillary scanner which avoids photobleaching of the sample in the capillary.

It is still a further object of this invention to provide a capillary array scanner in which the capillaries are shaped to provide a continuous sampling of the capillary volume.

These and other objects of the invention are achieved by a laser-excited capillary array scanner including a plurality of capillaries having a parallel, side-by-side, coplanar relationship and a laser-excited confocal fluorescence detector for detecting fluorescence from a selected interior volumes of each of said capillaries sequentially and repetitively during electrophoresis or other separation method. The invention also relates to a method of analyzing a plurality of capillaries, with a single scanner, by scanning a plurality of capillary passages in side-by-side relationship, and periodically and repetitively detecting fluorescence from each capillary passage during electrophoresis or any other separation procedure.

BRIEF DESCRIPTION OF THE DRAWINGS

The foregoing and other objects of the invention will be more clearly understood from the following description when read in connection with the accompanying drawings, wherein:

FIGS. 4A and 4B illustrate how the excitation beam is focused to a volume in the interior of a cylindrical capillary;

DESCRIPTION OF PREFERRED EMBODIMENT(s)

In accordance with this invention, the throughput in capillary electrophoresis is increased by employing a large number of capillaries in parallel. The most important problem confronting capillary array electrophoresis is detection. In copending patent application Ser. No. 07/531,900 filed Jun. 1, 1990, and incorporated herein by reference, there is described a laser-excited confocal fluorescence gel scanner which provides enhanced detection of fluorescently labelled DNA in slab gels. This detection system uses an epi-illumination format where the laser is focused on the sample by a microscope objective and the emitted fluorescence is gathered by the same objective using a 180° retro-optical geometry followed by confocal detection.

Sensitive detection of fluorescently-labeled analytes separated in small diameter capillaries is a difficult task. Because the capillaries have a 100 μm I.D. or less, a small focal volume is needed. The detection system must reject potentially strong Rayleigh scattering, fluorescence, and reflections from the capillary walls. Using confocal excitation and detection, the depth of field of the optical system is sufficiently small that only the interior of the 100 μm I.D. capillary is probed. The lateral resolution which is dictated by the scan stage and the laser beam diameter can be as small as a few microns. Background scattering and reflections from the capillary wall are rejected by the spatial and spectroscopic filters in front of the photodetector.

Figure 1:
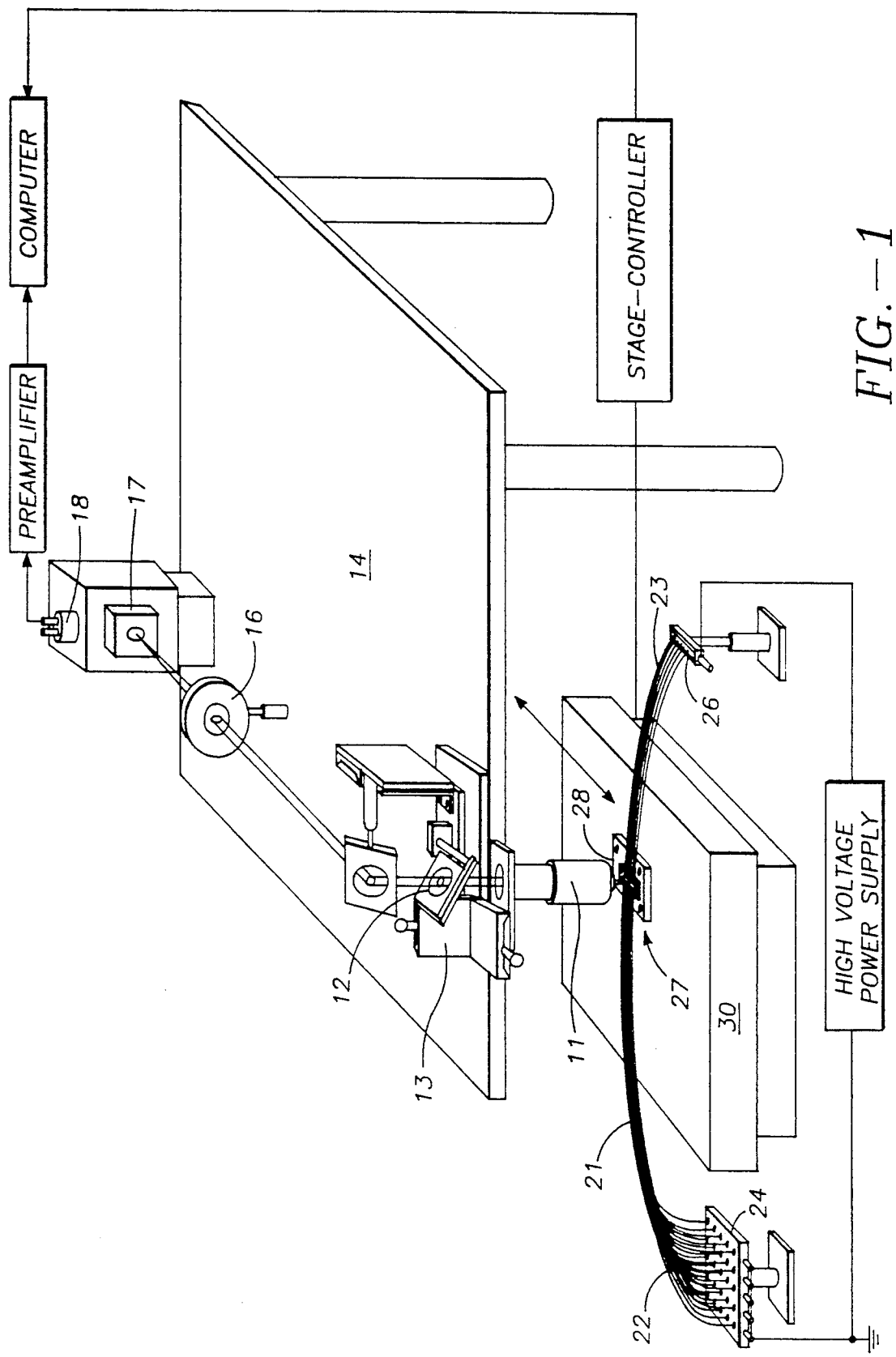
FIG. 1 is a schematic diagram of a confocal-fluorescence capillary array scanner in accordance with one embodiment of the invention.

A confocal fluorescence detection system for use with capillary arrays is shown in FIG. 1. An argon ion laser (Model 2020, Spectra-Physics, Mountain View, Calif.), not shown, is used as the excitation source. The laser beam is expanded to 5 mm diameter, collimated, and then directed through a 32×, N.A. 0.4 infinite conjugate objective 11 (LD Plan-Achromat 440850, Carl Zeiss, West Germany) by a long-pass dichroic beam-splitter 12 (480 DM, Omega Optical, Brattleboro, Vt.). The dichroic beam splitter 12 reflects the excitation laser beam into the objective 11 but transmits fluorescent light collected by the objective which is Stokes shifted to longer wavelengths. The objective focuses the exciting laser on the sample and gathers the fluorescence with very high collection efficiency. The use of an infinite conjugate objective permits vertical adjustment of the probe volume by translating the objective with the mount 13 secured to the base 14 with no significant perturbation of the optical alignment. The focused 1 mW, 488 nm wavelength beam is focused to a 10 μm beam diameter and a 25 μm confocal beam parameter. The fluorescence emission is passed back through the long-pass dichroic beam splitter 12 mounted on the base 14 to reduce laser interference and to separate the excitation and detection paths. The fluorescence is then focused by a 75 mm focal length lens 16 mounted on the base 14 onto a 400 μm pinhole which serves as the confocal spatial filter. The light passing through the pinhole is filtered by a 488 nm rejection band filter (488 RB filter, Omega Optical, Brattleboro, Vt.), a long-pass cutoff filter (Schott GG-495, Esco, Oakridge, N.J.), a bandpass fluorescence filter (530 DF60, Omega Optical, Brattleboro, Vt.), all mounted within the housing 17, followed by detection with a cooled photomultiplier tube 18 (RCA 31034A, Burle Industries, Lancaster, Pa.). The spatial filter, the optical filters and photomultiplier tube are mounted on base 14. The output of the phototube is amplified and filtered with a low-noise amplifier (SR560, Standford Research Systems, Sunnyvale, Calif.), digitized with a 12 bit analog-to-digital board (DASH-16 F, metra-Byte, Taunton, Mass.) and stored in an IBM PS/2 microcomputer. The electronic filter used for the phototube output was a first-order, active, low-pass filter (DC to 400 Hz) with a 12 dB/octave rolloff.

Figure 2:
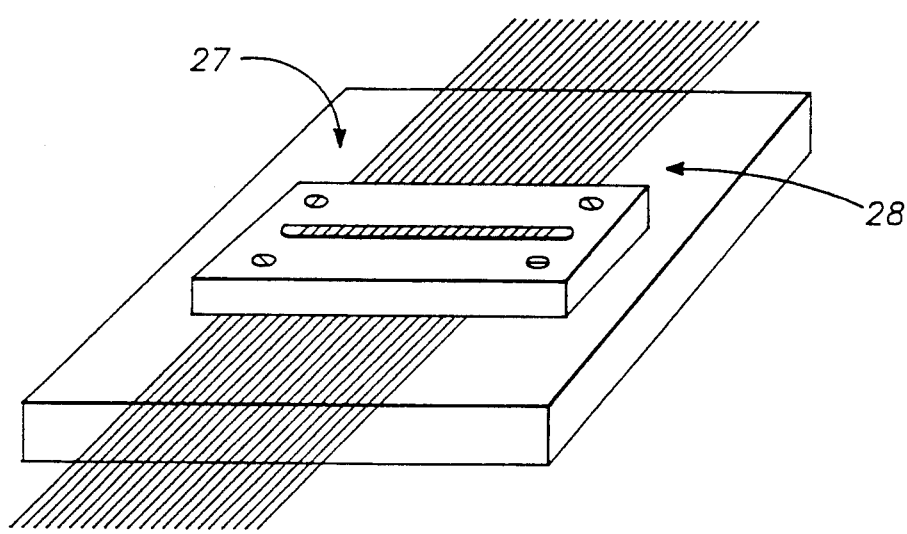
FIG. 2 is a view of a holder for supporting a region of the capillaries in side-by-side relationship.
Figure 3:
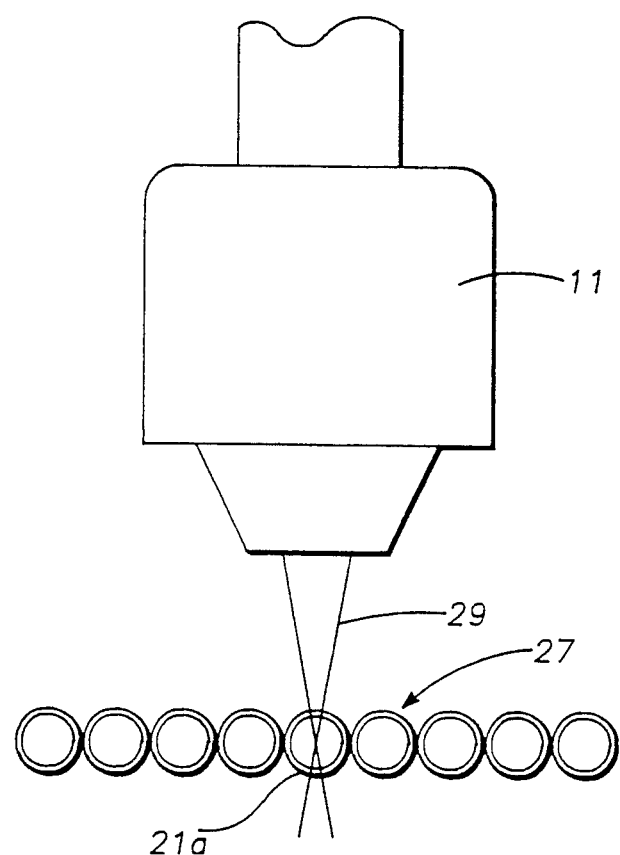
FIG. 3 is an enlarged view of the focal zone.

The capillary array comprises a plurality of capillaries 21 having their ends 22,23 extending into wells 24, 26 between which a high voltage is applied for electrophoresis. The ends 22 may be separated for individual manipulation and loading. A portion 27 of the capillaries is maintained in side-by-side parallel coplanar relationship by a holder 28, FIG. 2. The holder 28 includes a window through which the beam can be focused on the interior volume of the capillaries. FIG. 3 shows the beam 29 focused in an interior volume of a capillary 21a.

For several reasons, scanning the beam and detection system across the capillary is *better* than just probing in the center of the capillary. First, if the probe laser is fixed at the center of the capillary, the sample stream will be rapidly photo-bleached by the laser. Scanning the beam laterally across the capillary interior is much better than sitting in one spot because all of the band is probed (laterally) and photo-bleaching is reduced. Also, the off-axis probing is advantageous because, as shown in FIGS. 4A and 4B, the cylindrical lens effect actually brings the beam waist back into the capillary gel so the detection system probes the gel for a longer period of time during the scan than would have been nominally predicted from the capillary diameter and scan rate.

The holder 28 is mounted on a translation stage 30 (Model 4000, Design Components, Franklin, Mass.). The stage is programmed to continuously scan the capillary array back and forth at 20 mm/sec in a direction perpendicular to the electrophoresis direction. The image acquired in this way has two dimensions. One is a spatial dimension representing the physical image of the capillaries. The other is a temporal dimension proportional to the elapsed time. During a particular sweep, fluorescence data from the photodetector is sampled at 2000 Hz so the nominal image resolution is 10 µm/pixel; thus, 10 pixels represent the interior 100 µm width of any given capillary. The electronic low-pass filter cutoff was set at 300 Hz to provide high frequency noise rejection while still passing the spatial frequencies required to define the 100 µm I.D. of the capillaries. An image of the migrating bands is built up as a function of time by accumulating periodic one-second sweeps of the illuminated region of the capillaries. The transit time of the migrating DNA past the probe region, under the conditions employed here, ranges from approximately 10 seconds for the low molecular weight fragments (40–50 mers) to 14 seconds for the higher molecular weight fragments (380–390 mers). With one-second repeat cycles, this gives 10–14 samples of each band. The computer processes the data and displays the acquired image in real time. Image processing can be performed with the NIH program, Image 1.29, and commercial image processing package, Canvas TM, to provide an image, FIG. 5. The image data can be reduced to a one-dimensional line plot or electropherogram by averaging the pixels across the width of each lane using Image 1.29, FIGS. 6(A–D), and sections can be expanded as shown in FIGS. 7(A–D).

In one example, zero-crosslinked polyacrylamide gel-filled capillaries were prepared using a modified method of the procedure described by Cohen, et al.[6,7]. A 3 mm wide detection window was produced in each 100 µm I.D. 200 µm O.D. fused-silica capillaries (Polymicro Technologies, Phoenix, Ariz.) by burning off the polyimide coating with a hot wire. The window was burned ~25 cm from the inlet side of the 40 cm long capillary. The inner wall of the capillaries was then treated overnight with a bifunctional reagent, γ-methacryloxypropyltrimethoxy-silane to prepare the walls for acrylamide adhesion[6]. Freshly-made acrylamide gel solution (9% T, 0% C) in a 1X TBE buffer (tris-boric acid-EDTA) with 7 M urea was filtered with an 0.2 µm syringe filter and degassed under vacuum for about one hour. 10% TEMED (tetraethylmethylenediamine) and 10% APS (ammonium persulfate) solution were added to the gel solution at a final concentration of approximately 0.03%. The solution was immediately vacuum siphoned into the capillaries and then allowed to polymerize overnight in a cold room. Prior to use, both ends of the column were trimmed by about 1 cm and then pre-electrophoresed for 30 to 60 minutes at 7 kV.

The capillary array was sandwiched in the capillary holder 28 that is mounted onto the translation stage 30. The capillary holder 28, FIG. 2, serves the dual purpose of (1) uniformly constraining each capillary in the array to an identical height above the top of the translation stage, and (2) exposing a small window through which the confocal zone probed the capillary interior. Constraining the capillaries to substantially the same plane is necessary for achieving uniform detection sensitivity from each capillary because the depth of focus of the microscope objective is only ~25–50 µm.

The DNA samples for which the data is shown in FIGS. 5–7D was prepared as follows: chain-terminated M13mp18 DNA fragments were generated using a Sequenase 2.0 sequencing kit (U.S. Biochemical Corp., Cleveland, Ohio) and fluorescein-tagged primer "FAM" (Applied Biosystems, Foster City, Calif.). The detailed procedure has been published elsewhere[25]. Briefly, about one pmol of the primer and single-stranded M13mp18DNA were heated to 65° C. for three minutes and then allowed to cool (annealing reaction). Meanwhile, the sequencing extension mixture was added into a centrifuge tube followed by addition of the dideoxy termination mixture. When the temperature of the annealing reaction mixture drops below 30° C., a combination of the labeling mixture and diluted enzyme (Sequenase 2.0 TM) were added, and the mixture was incubated for five minutes at room temperature. This mixture was then transferred to the tube having the termination mixture and allowed to incubate for another five minutes at 37° C. Instead of adding stop solution, ethanol precipitation was immediately used to terminate the reaction and recover the DNA sequencing sample. The high concentration of conductive ions present in the DNA sequencing sample after the termination step would reduce the amount of DNA that can be loaded into each capillary by electrokinetic injection. To counteract this effect, ethanol precipitation was performed on all DNA samples followed by resuspension in 6 µl of 80% (v/v) formamide to give a concentration about ten-fold higher than that used in slab gels. The sample was heated at 90° C. for three minutes to ensure denaturation and then placed on ice until sample injection.

The flexibility of the capillary columns allows coupling of the individual capillaries of the array to individual sample wells. In the foregoing example, since only one DNA sequencing sample was run, the sample was placed in a single 500 μl centrifuge tube for electrokinetic injection into the capillaries. The same electric field strength (200 volt/cm) used during separation was also applied during sample injection. The typical injection time was ten seconds. After injection, the inlets of the capillaries were removed from the centrifuge tube and placed into a buffer reservoir or well 24 filled with fresh running buffer. The 9T gels are sufficiently stable that four to five sequencing runs could be run on each capillary.

Figure 5:
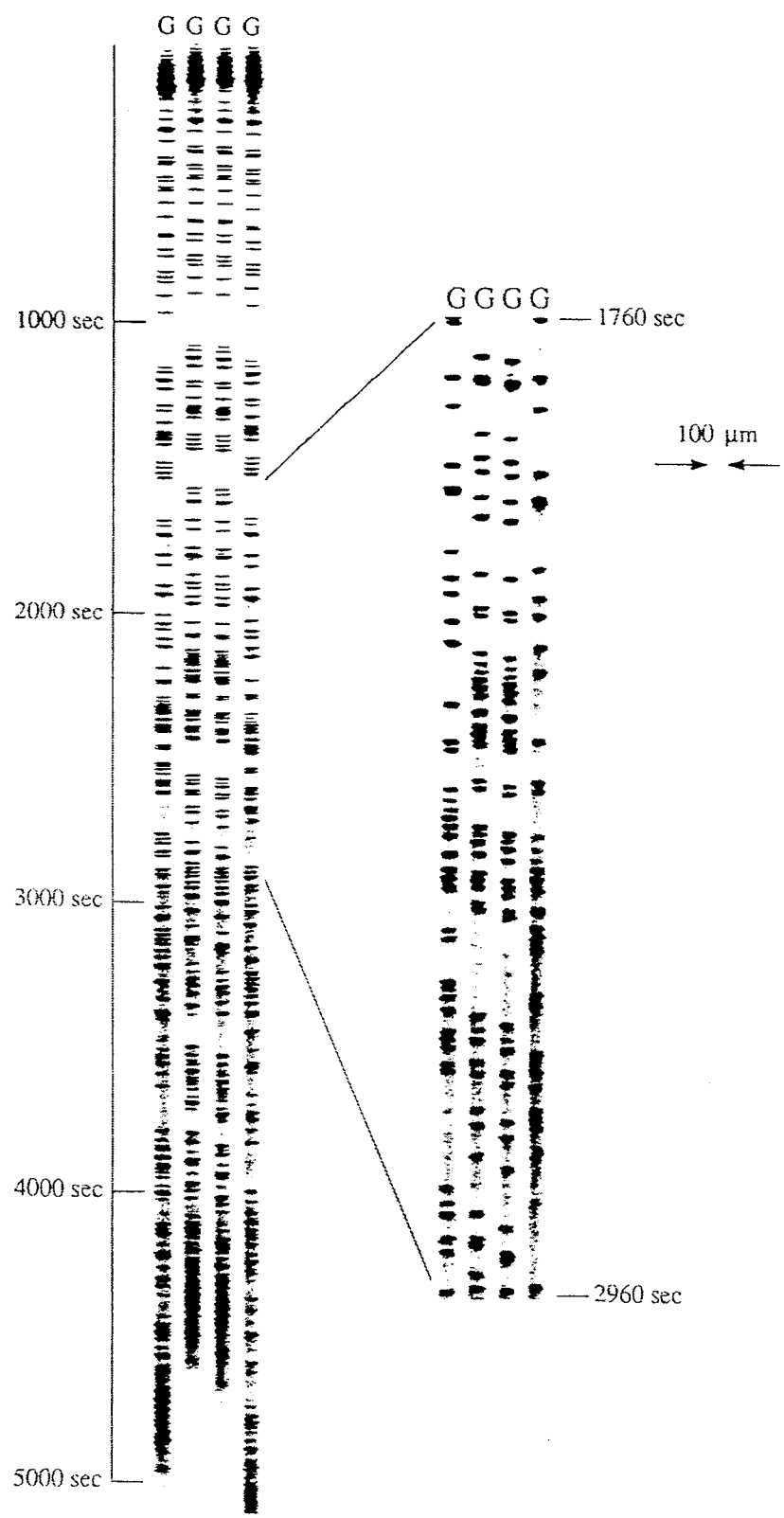
FIG. 5 is an image obtained by scanning a four-capillary array during a DNA separation.

FIG. 5 presents an image obtained from on-line confocal scanning of a four-capillary array during electrophoresis of a mixture of DNA sequencing fragments. The horizontal direction is the physical dimension representing the geometric arrangement of the array while the vertical direction is temporal, representing the passage of fluorescent DNA fragments through the detection window. For lane-to-lane comparison, identical samples of "G" base DNA fragments were simultaneously, electrokinetically injected into each capillary. The overall elapsed data acquisition time is ~80 minutes after passage of the primer. An expanded region of the image is included in FIG. 5. The bands in all four lanes are well resolved and the resolution extends throughout the sequencing run with sufficient signal-to-noise to detect bands more than 500 bases beyond the primer. From FIG. 5, one can clearly see that the cylindrical capillaries do not significantly distort the image.

Figure 6C:
FIGS. 6 (A-D) are an electropherogram of the DNA separation of FIG. 5.
Figure 6D:
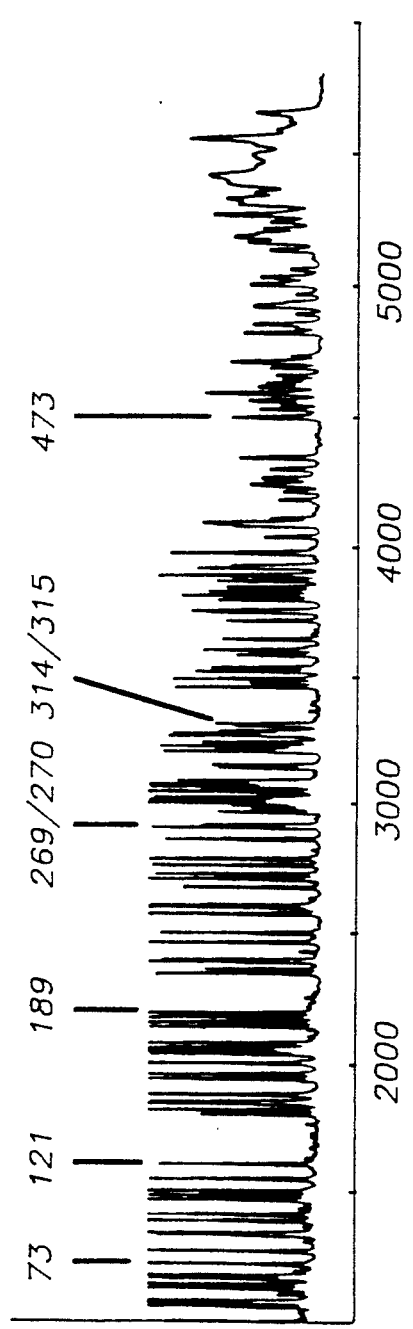
Figure 7C:
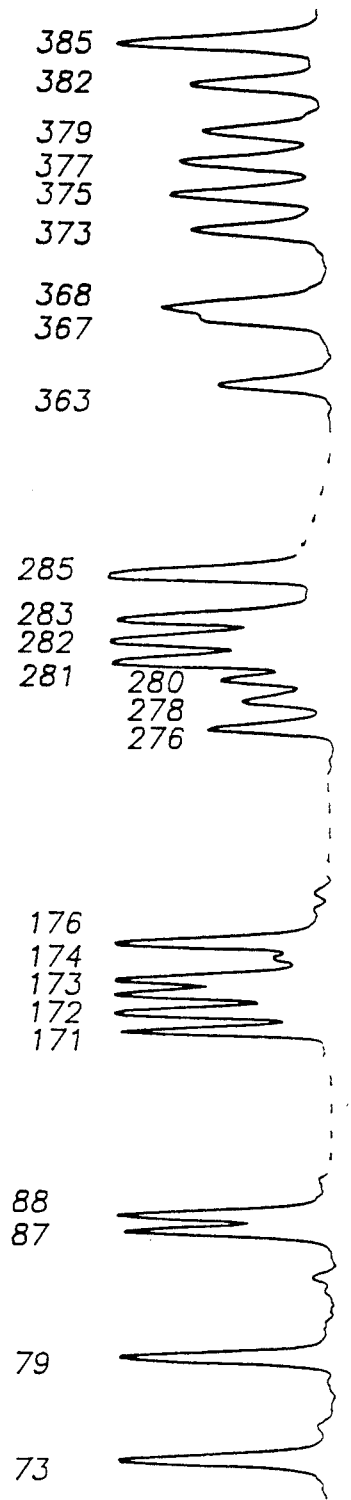
FIGS. 7 (A-D) are an expanded view of the indicated regions of the electropherograms of FIGS. 6 (A-D)
Figure 7D:
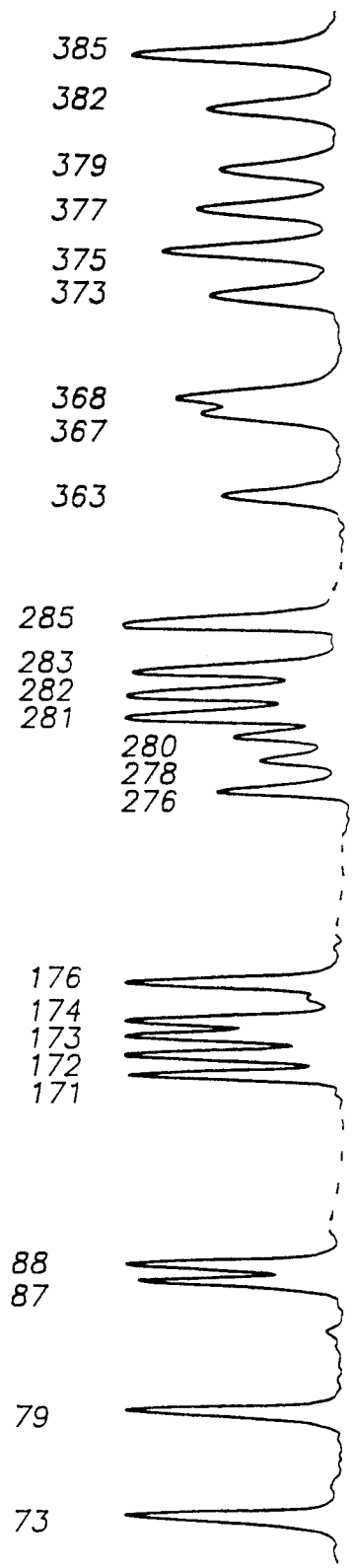

FIGS. 6(A-D) and 7(A-D) present line plots of the DNA signal integrated across the width of each capillary. A signal-to-noise ratio of approximately 20 is observed out to base 385 (~65 minutes) and bands are detected out to base 500 with the present experimental conditions. The number of theoretical plates is $>1.9\times 10^6$ (at base 385) over a 24 cm effective column length.

A comparison was made between the signal-to-noise ratio obtained in the scanning mode and the case where the system is focused in the center of a single stationary capillary. The latter approach is analogous to traditional on-column detection from a single capillary. The sensitivity limits extrapolated for the scanning mode were found to be $\sim 2\times 10^{-12}$M (S/N=3) by flowing $1\times 10^{-11}$M fluorescein through an open capillary. The sensitivity limits for the stationary mode were found to be $\sim 1\times 10^{-12}$M. These detection limits are at least as good as those reported from single capillaries using the conventional 90° detection geometry[10]. The background from the gel-filled capillaries was ~2.6 times (n=4) higher than that from a capillary filled with just TBE buffer. Thus, the presence of the gel increased the background noise by a factor of ~1.6.

This work indicates that the overall throughput performance of CAE can be very high. In the present study, satisfactory sequencing information is obtained out to 500 bases for each of four capillaries. The overall throughput of the system depends upon the total number of capillaries, N, that can be scanned. The equation, NvT/2D, defines how N depends on the scan speed (v), the scan repetition period (T), and the capillary outside diameter (D). For example, one hundred 200 μm wide capillaries can be easily seen using a scan rate of four cm/sec and a one-sec scan repetition period. Increasing the array size would require (1) an increase in the scan speed; (2) the use of smaller O.D. capillaries; and (3) an increase in the scan repetition period which would reduce the temporal resolution of the electrophoretic separation. Since reliable systems have velocities up to ten cm/sec and capillaries with O.D.'s of 150 μm are commercially available, a limit of approximately 330 capillaries/array can be projected, assuming a one-second scan repetition period.

Figure 8:
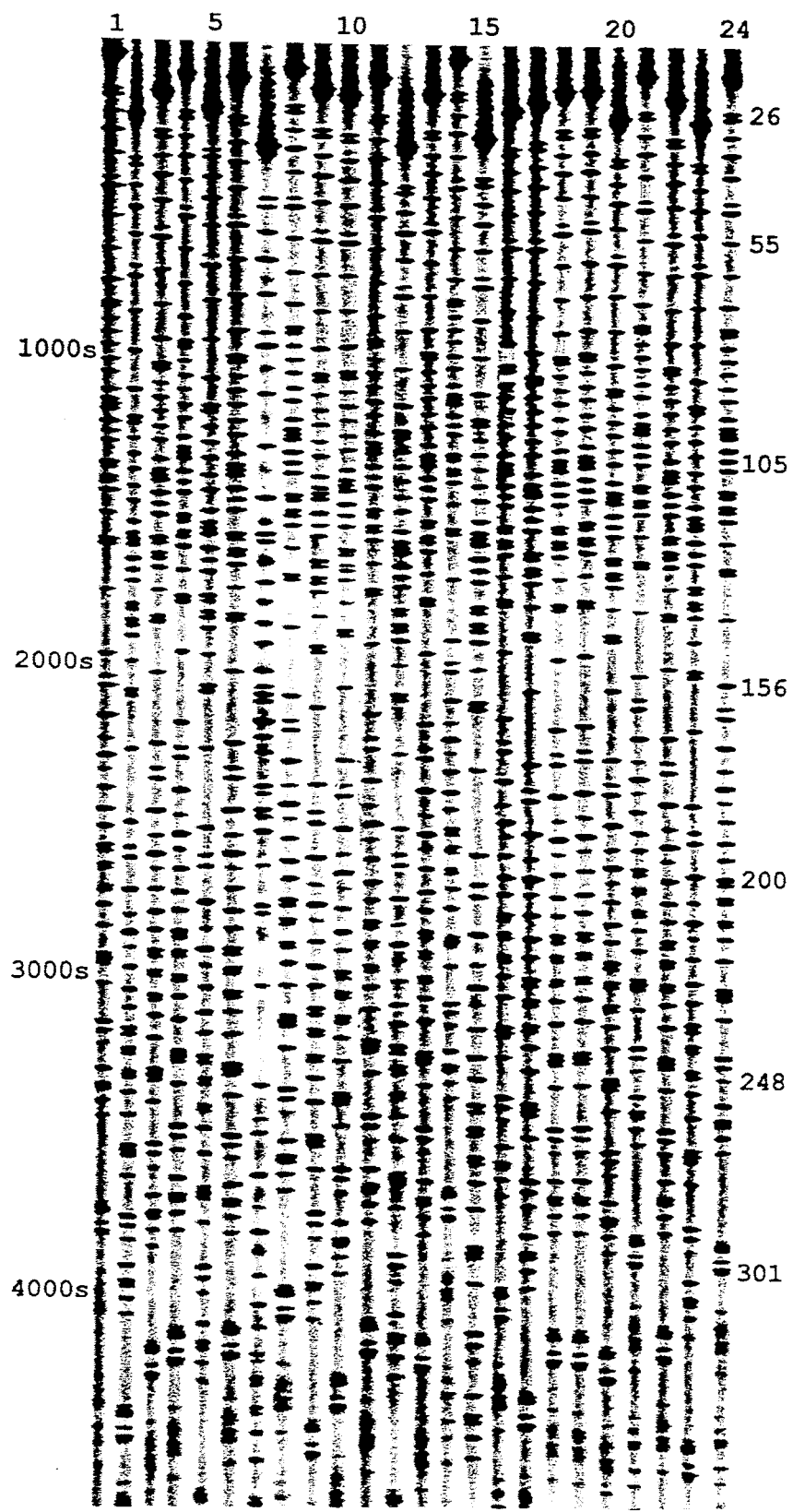
FIG. 8 is an image obtained by scanning a twenty-four capillary array.

To illustrate our ability to extend this system to large numbers of capillaries we present, in FIG. 8, an array of 24 capillaries that have been used to separate a different DNA sequencing sample.

Finally, it should be noted that there is a significant difference in the migration time of a given DNA band from lane-to-lane. This may be caused by inhomogeneities of the gel matrix or the presence of local non-uniform variations in the electric field strength. It has previously been estimated that there is a 5% variation in migration time between identical samples on different gel columns[4].

The velocity shift of the DNA bands from lane-to-lane may preclude sequencing DNA with CAE using a single fluorophore and four different capillaries, one for each base. For DNA sequencing, the present apparatus must be expanded to a multi-color detection system to sequence all four bases in a single capillary. Such four-color detection schemes have been developed for single capillaries[8] and for slab gels[19]. The basic idea is that one is separating four sets of DNA fragments which terminate with either a G, A, T or C. Each set is labeled with a different fluorescent tag by any of several procedures and then the fragment sets are pooled and separated on the same capillary. If the fluorescent tags emit in a sufficiently distinctive wavelength region, the four sets of fragments can be uniquely detected by using a four-color detection system.

Figure 9:
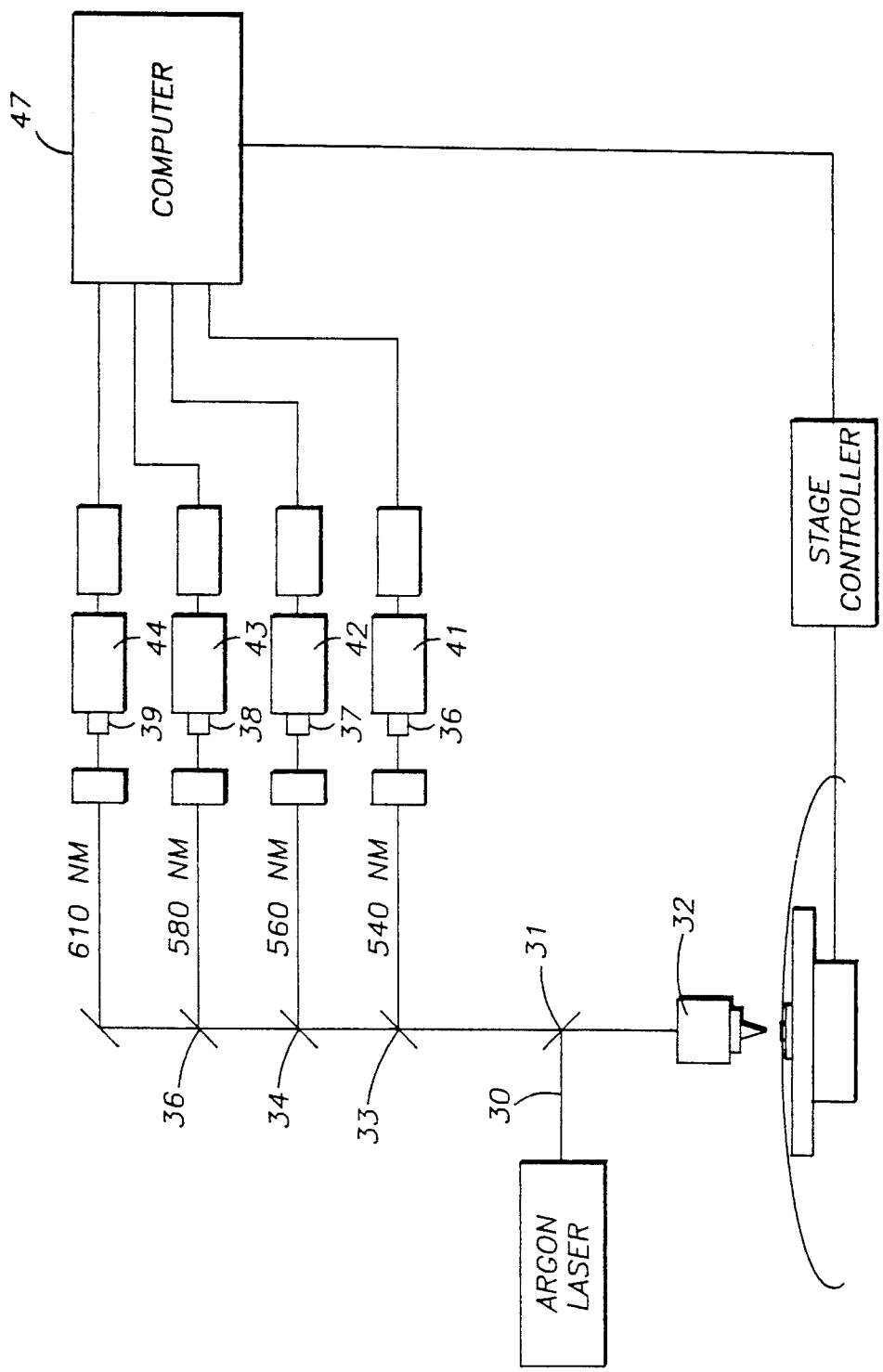
FIG. 9 is a schematic diagram of a four-color confocal-fluorescence capillary scanner.

A schematic diagram of a four-color confocal fluorescence capillary array scanner is shown in FIG. 9. The scanner includes a laser source such as an argon laser which projects a beam 30 into the dichroic beamsplitter 31 which directs the beam to the objective 32. The objective collects the fluorescent energy from the focal volume and directs it through the beamsplitter. The output of the beam splitter is directed to a first beam splitter 33 which reflects energy at one wavelength, for example, 540 μm, and passes other, longer wavelengths. The next dichroic beamsplitter 34, which reflects energy at a second wavelength, for example, 560 μm, and passes other, longer wavelengths. A third beamsplitter 36 reflects energy at another wavelength, for example, 580 μm, and passes energy at 610 μm. The energy from each of the beamsplitters 33, 34, and 36 and the transmitted energy is applied to confocal, spatial and spectrial filters 37, 38, 39 to photomultipliers 41, 42, 43 and 44 which provide output signals that are processed and applied to computer 47 which generates an image for each of the wavelengths, for each of the capillaries. Each color image then records the passage of a particular labeled set of DNA sequencing fragments through the detection zone—one color for the A-fragments, a second for the G-fragments, a third for the T-fragments and a fourth for the C-fragments.

Throughout the preceding description and drawings, reference has been made to capillary arrays. It should be recognized that even though capillary arrays comprising a plurality of capillary tubes have been shown and discussed that it is possible to form parallel capillary passages in a block of material by photoetching, micromachining, casting and other techniques used in the semiconductor industry. Thus, capillary array as used herein is meant to encompass all types of capillary passages arranged in an array.

The preceding description is based on continuous scanning across the capillary array. In some applications, it may be desirable to focus sequentially at the center of each capillary and step between capillaries. Finally, it is possible to scan across each capillary to scan the band, but then rapidly step or move to the next capillary.

In summary, it has been shown that it is possible to perform high-sensitivity fluorescence detection of capillary arrays using a confocal fluorescence scanner. This format has the advantages that (1) many analytes can be run in parallel; (2) loading multiple samples can be easily accomplished; (3) rapid separations are achieved; and (4) the detection sensitivity is excellent. Use of capillary arrays resolves the fundamental throughput problems that limit the utility of CE in, for example, DNA sequencing[28]. In addition, CAE provides an opportunity for the large-scale optimization of analytical separations. A large number of capillaries can be run in parallel each with a different buffer pH, buffer composition, or load to determine the best separation conditions. Commercially made capillary arrays could be constructed which plug into multi-well devices for large-scale parallel sample introduction. CAE should be a valuable new technique for rapid, parallel separation and analysis. The apparatus has been described in connection with capillary array electrophoresis. However, it is to be understood that it can be used in connection with other types of capillary separations, such as capillary chromatography, isoelectric focusing and column derivations.

The foregoing descriptions of specific embodiments of this invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best use the invention and various embodiments with various modifications as are suited to the particular use contemplated. It is intended that the scope of the invention be defined by the claims appended hereto and their equivalents.

Jorgenson, J. W.; Lukacs, K. D.; *Science* 1983, 222, 266–272
Gordon, M. J.; Huang, X.; Pentoney, S. L., Jr.; Zare, R. N.; *Science* 1988, 242, 224–228
Ewing, A. G.; Wallingford, R. A.; Olefirowicz, T. M.; *Anal. Chem.* 1989, 61, 292A–303A
Karger, B. L.; Cohen, A. S.; Guttman, A.; *J. Chromatogr.* 1989, 492, 585–614
Kuhr, W. G.; *Anal. Chem.* 1990, 62, 405R–414R
Cohen, A. S.; Najarian, D. R.; Paulus, A.; Guttman, A.; Smith, J. A.; Karger, B. L.; *Proc. Natl. Acad. Sci. USA*, 1988, 85, 9660–9663
Heiger, D. N.; Cohen, A. S.; Karger, B. L.; *J. Chromatogr.* 1990, 516, 33–48
Luckey, J. A.; Drossman, H.; Kostichka, A. J.; Mead, D. A.; D'Cunha, J.; Norris, T. B.; Smith, L. M.; *Nucleic Acids Res.* 1990, 18 4417–4421
Swerdlow, H.; Wu, S.; Harke, H.; Dovichi, N. J.; *J. Chromatogr.* 1990, 516, 61–67
Swerdlow, H.; Gesteland. R.; *Nucleic Acids Res.* 1990, 18, 1415–1419
Drossman, H.; Luckey, J. A.; Kostichka, A. J.; D'Cunha, J.; Smith, L. M.; *Anal. Chem.* 1990, 62, 900–903
Compton, S. W.; Brownlee, R. G.; *Bio Techniques* 1988, 6, 432–439
Cohen, A. S.; Najarian, D.; Smith, J. A.; Karger, B. L.; *J. Chromatogr.* 1988, 458, 323–333
Cheng, Y. F.; Dovichi, N. J.; *Science* 1988, 242 562–564
Hjerten, S.; Elenbring, K.; Kilar, F.; Liao, J. L.; Chen, A. J. C.; Sieberg, C. J.; Zhu, M. D.; *J. Chromatogr.* 1987, 403, 47–61
Gassmann, E.; Kuo, J. E.; Zare, R. N.; *Science* 1985, 230, 813–814
Ansorge, W.; Sproat, B.; Stegemann, J.; Schwager, C.; Zenke, M.; *Nucleic Acids Res.* 1987, 15, 4593–4602
Brumbaugh, J. A.; Middendorf, L. R.; Grone, D. L.; Ruth, J. L.; *Proc. Natl. Acad. Sci. USA* 1988, 85, 5610–5614
Smith, L. M.; Sanders, J. Z.; Kaiser, R. J.; Hughes, P.; Dodd, C.; Connell, C. R.; Heiner, C.; Kent, S. B. H.; Hood, L. E.; *Nature* 1986, 321, 674–679
Zagursky, R. J.; McCormick, R. M.; *Bio Techniques* 1990, 9, 74–79
Prober, J. M.; Trainor, G. L.; Dam, R. J.; Hobbs, F. W.; Robertson, C. W.; Zagursky, R. J.; Cocuzza, A. J.; Jensen, M. A.; Baumeister, K.; *Science* 1987, 238, 336–341
Glazer, A. N.; Peck, K.; Mathies, R. A.; *Proc. Natl. Acad. Sci. USA* 1990, 87, 3851–3855
Mathies, R. A.; Peck, K.; Stryer, L.; *Bioimaging and Two-Dimensional Spectroscopy*, L. C. Smith (ed.), SPIE-The International Society for Optical Engineering, Bellingham, Wash. 1990, 52–59
Rye, J. S.; Quesada, M. A.; Peck, K.; Mathies, R. A.; Glazer, A. N.; *Nucleic Acids Res.* 1991, 19, 327–333
Quesada, M. A.; Rye, H. S.; Gingrich, J. C.; Glazer, A. N.; Mathies, R. A.; *Bio Techniques* 1991, 10 616–625
L. Hernandez, R. Marquina, J. Escalona, N. A. Guzman, *J. Chromatogr.* 502, 247–255 (1990).
L. Hernandez, J. Escalona, N. Joshi, N. Guzman, *J. Chromatogr.* 559, 183–196
Smith, L. M.; *Nature* 1991, 349, 812–813

What is claimed:

1. A scanner for exciting and detecting radiation from a plurality of adjacent capillary passages comprising
   a plurality of side-by-side capillary passages disposed in a plane,
   a source of radiant energy of a first wavelength,
   an objective lens for receiving and focusing said radiant energy at an excitation volume in the plane of said plurality of side-by-side capillary passages,
   means for moving said plurality of side-by-side capillary passages so that said excitation volume sequentially and repetitively is within one of said plurality of side-by-side capillary passages to excite material in said one passage and cause the material to radiate energy at a different wavelength,
   said objective lens serving to collect the radiated energy of said different wavelength and direct it to an optical system which includes confocal spatial and spectral filter means to transmit said radiated energy at said different wavelength and reject radiation at other wavelengths,
   a detection system for receiving said radiated energy and generating a signal, and
   computer means for receiving and processing said signal to provide an output representative of the material at the excitation volume in each of said plurality of side-by-side capillary passages.

2. A scanner as in claim 1 in which said means for moving said plurality of side-by-side capillary passages is controlled by said computer, whereby the output is correlated with the individual passages in said plurality of side-by-side capillary passages.

3. A scanner as in claim 2 in which each of the capillary passages of the plurality of side-by-side capillary passages is part of an elongated cylindrical capillary.

4. A scanner as in claim 3 including means for holding a region of the cylindrical capillaries in side-by-side co-planar relationship for presentation to the focused radiant energy.

5. A scanner as in claim 4 in which the ends of said capillaries are separable for individual manipulation and loading.

6. A scanner as in claim 1 in which said means for moving the plurality of side-by-side capillary passages moves them continuously whereby to scan a band in each capillary of said plurality of side-by-side capillary passages.

7. A scanner as in claim 1 in which said means for moving said plurality of side-by-side capillary passages steps the individual capillary passages into said excitation volume.

8. An apparatus for exciting and detecting radiation from sample material in capillary passages comprising
   means for presenting a plurality of capillary passages in side-by-side coplanar relationship,
   radiation means for exciting sample material in said plurality of side-by-side coplanar capillary passages with radiation of a first wavelength;
   means for moving said plurality of side-by-side coplanar capillary passages to sequentially and repetitively excite sample material in each passage of said plurality of side-by-side coplanar capillary passages with said radiation,
   means for collecting radiation emitted from said sample material,
   means for detecting radiation emitted by the sample material in said plurality of side-by-side coplanar capillary passages responsive to said radiation at a first wavelength, and
   computer means for processing the detected emitted radiation and for controlling said moving means to providing a two-dimensional output representative of the sample material in said plurality of side-by-side coplanar capillary passages as a function of time and position.

9. A scanner as in claim 8 in which each of said capillary passages of said plurality of said capillary passages is part of an elongated cylindrical capillary.

10. A scanner as in claim 9 including means for holding a region of said elongated cylindrical capillaries in side-by-side coplanar relationship for presentation to the radiant energy.

11. A scanner as in claim 8 in which the ends of said cylindrical capillaries is independently manipulatable.

12. A scanner for detection of fluorescently labeled analytes which can be separated in small diameter capillaries comprising
   a plurality of capillaries each for separating a fluorescently labeled analyte
   a source of radiant energy having an excitation wavelength which excites fluorescence from said labeled analyte,
   lens means for focusing said radiant energy to a small volume and for collecting fluorescence from said volume
   means for sequentially and repetitively presenting a region of said plurality of capillaries to said small volume of radiant energy whereby to cause fluorescence of the fluorescently labeled analyte at said volume, and;
   means for receiving the collected fluorescence and providing an output representative of the analyte at said small volume of the presented region of said plurality of capillaries.

13. A scanner as in claim 12 in which said lens means comprises an objective lens forming a part of a confocal optical detection assembly including a spatial filter.

14. A scanner as in claim 13 in which said optical detection system includes spectral filters for rejecting energy at said excitation wavelength.

15. A method of detecting fluorescence from DNA sequencing fragments electrophoretically separated in a plurality of capillaries which comprises positioning a region of said plurality of capillaries in side-by-side coplanar relationship
exciting a predetermined volume sequentially and repetitively in individual capillaries with light energy of predetermined wavelength focused therein by an objective lens to cause fragments to fluoresce and emit light at a different wavelength,
collecting the fluorescently emitted light from said predetermined volumes in each of said capillaries with said objective lens,
spectrally and spatially filtering said fluorescently emitted light of different wavelength to reject light at said predetermined wavelength and pass said fluorescently emitted light; and,
applying the filtered fluorescently emitted light to a detector to generate an output signal representative of the fluorescence from said fragments in said predetermined volume in each of said capillaries.

16. The method of claim 15 in which the ends of the capillaries are separated for rapid parallel loading of sequencing fragments into the capillaries.

17. A scanner for exciting and detecting radiation from a plurality of adjacent capillary passages comprising
   a plurality of side-by-side capillary passages disposed in a plane,
   a source of radiant energy of a first wavelength,
   an objective lens for receiving and focusing said radiant energy at an excitation volume in the plane of said passages,
   a beamsplitter for directing said radiant energy to the objective lens to excite said excitation volume with energy at said first wavelength,
   means for moving said passages so that said excitation volume sequentially and repetitively is within one of said plurality of side-by-side capillary passages to excite material in said passage and cause the material to radiate energy at a different wavelength,
   said objective lens serving to collect said the radiated energy of said different wavelength and direct it through said beamsplitter which passes radiated energy at said different wavelength to an optical system which includes a confocal spatial filter and spectral filter to transmit said radiated energy at said different wavelength and reject radiation at other wavelengths,
   a detection system for receiving said radiated energy and generating a signal, and
   computer means for receiving and processing said signal to provide an output representative of the material at the excitation volume in each of said plurality of side-by-side capillary passages.

18. A scanner as in claim 17 in which said means for moving said passages is controlled by said computer, whereby the output is correlated with each of said capillary passages of said plurality of side-by-side capillary passages.

19. A scanner as in claim 18 in which said means for moving the plurality of side-by-side capillary passages moves said plurality of side-by-side capillary passages continuously whereby to scan a band in each of said capillary passages.

20. A scanner as in claim 18 in which each of the capillary passages of said plurality of side-by-side capillary passages is part of an elongated cylindrical capillary.

21. A scanner as in claim 20 including means for holding a region of the cylindrical capillaries in side-by-side co-planar relationship for presentation to the focused radiant energy.

22. A scanner as in claim 21 in which the ends of said cylindrical capillaries is separable for individual manipulation and loading.

23. A scanner as in claim 17 in which said means for moving said plurality of side-by-side capillary passages steps the plurality of side-by-side capillary passages into said excitation volume.

24. A method of detecting fluorescence from DNA sequencing fragments electrophoretically separated in a plurality of capillaries which comprises positioning a region of said plurality of capillaries in side-by-side coplanar relationship exciting a predetermined volume in each of said capillaries sequentially and repetitively with light energy of predetermined wavelength focused therein by an objective lens to cause fragments to fluoresce and emit light at a different wavelength, collecting the fluorescently emitted light from said predetermined volumes in each of said capillaries with said objective lens, spectrally and spatially filtering said fluorescently emitted light energy of different wavelength to reject light at said predetermined wavelength and scattered light, and pass said emitted light of different wavelength; and, applying the filtered emitted light of different wavelength to a detector to generate an output signal representative of the fluorescence from said fragments in said volume of each of said capillaries.

25. The method of claim 24 in which the ends of the capillaries are separated for rapid parallel loading of sequencing fragments into the capillaries.

26. A scanner for exciting and detecting radiation from a plurality of adjacent capillary passages comprising a plurality of side-by-side capillary passages disposed in a plane, a source of radiant energy of a first wavelength, an objective lens for receiving and focusing said radiant energy at an excitation volume in the plane of said plurality of side-by-side capillary passages, means for moving said plurality of side-by-side capillary passages so that said excitation volume sequentially and repetitively is within one of said plurality of side-by-side capillary passages to excite material in said one passage and cause the material to radiate energy at a plurality of different wavelengths, said objective lens serving to collect the radiated energy of said different wavelengths and direct it to an optical system including a plurality of dichroic beam splitters for selectively directing the radiated energy of each of said different wavelengths to a different location, a plurality of sets of spatial and spectral filter means one for each of said different wavelengths, and a plurality of detection means, one for each set of spatial and spectral filter means, for receiving the radiated energy of each different wavelength and providing corresponding output signals, and computer means for receiving and processing said signals to provide an output representative of the material at the excitation volume in each of said plurality of side-by-side capillary passages.

27. A scanner for exciting and detecting radiation from a plurality of adjacent capillary passages comprising a plurality of side-by-side capillary passages disposed in a plane, a source of radiant energy of a first wavelength, an objective lens for receiving and focusing said radiant energy at an excitation volume in the plane of said passages, a beamsplitter for directing said radiant energy to the objective lens to excite said excitation volume with energy at said first wavelength, means for moving said passages so that said excitation volume sequentially and repetitively is within one of said plurality of side-by-side capillary passages to excite material in said passage and cause the material to radiate energy at different wavelengths, said objective lens serving to collect the radiated energy of said different wavelengths and direct it through said beamsplitter which passes radiated energy at said different wavelengths to an optical system which includes a plurality of additional beamsplitters, spatial and spectral filter means for selectively directing the radiated emitted energy of different wavelengths to different locations and a plurality of detection means each receiving emitted energy at one of said different wavelengths and providing corresponding output signals, and computer means for receiving and processing said signals to provide an output representative of the material at the excitation volume in each of said plurality of side-by-side capillary passages.

28. A method of detecting fluorescence from DNA sequencing fragments electrophoretically separated in a plurality of capillaries which comprises positioning a region of said plurality of capillaries in side-by-side coplanar relationship, exciting a predetermined volume in each of said capillaries sequentially and repetitively with light energy of predetermined wavelength focused therein by an objective lens to cause fragments to fluoresce and emit light at different wavelengths, collecting the fluorescently emitted light at different wavelengths from said predetermined volumes in each of said capillaries with said objective lens, spectrally and spatially filtering said fluorescently emitted light energy of different wavelengths to reject light at said predetermined wavelength and scattered light, and pass said emitted light of different wavelengths; and, applying the filtered emitted light of different wavelengths to detectors to generate an output signal representative of the fluorescence from said fragments in said volume of each of said capillaries at each of said different wavelengths.

* * * * *

UNITED STATES PATENT AND TRADEMARK OFFICE
CERTIFICATE OF CORRECTION

PATENT NO. : 5,274,240

DATED : December 28, 1993

INVENTOR(S) : Richard A. Mathies et al.

It is certified that error appears in the above-identified patent and that said Letters Patent is hereby corrected as shown below:

On the title page, item [56] References Cited:

Under U.S. Patent Documents, line 12, amend "Yueng et al" to --Yeung et al.--

Under Other Publications, line 9, after "Detection" insert --"--

On page 2:

Column 1, line 11, change "405R" to --403R--

Column 1, line 16, change "96633." to --9663.--

Column 1, line 43, change "Sieberg," to --Siebert,--

Column 1, line 45, change "Electrophorsis" to --Electrophoresis--

Column 2, line 30, change "confocal" to --Confocal--

Column 2, line 32, change "10 616-625" to --10, 616-625.--

Column 1, line 6, change "DIR-87-20382" to --BBS-87-20382

Column 1, line 9, change "Department of Defense" to --Department of Energy--

Column 1, line 56, change "throughout" to --throughput--

Column 2, line 21, change "gels$^{22-26}$" to --gels$^{22-25}$--

Column 2, line 27, change "of a field" to --of field--

Column 2, line 30, after "reflections from" insert --the--

UNITED STATES PATENT AND TRADEMARK OFFICE
CERTIFICATE OF CORRECTION

PATENT NO. :   5,274,240

DATED      :   December 28, 1993

INVENTOR(S) :  Richard A. Mathies et al.

It is certified that error appears in the above-identified patent and that said Letters Patent is hereby corrected as shown below:

Column 2, line 34, change "high quality" to --high-quality--

Column 2, line 37, change "capillaries $^{27,28}$" to --capillaries $^{26,27}$--

Column 3, line 40, after "from" delete --a--

Column 3, line 67, change "are an electropherogram" to --are Electropherograms--

Column 4, line 1, change "are an expanded view" to --are expanded views--

Column 4, line 28, after "scattering", insert --stray--

Column 5, line 11, change "microcomputer" to --computer--

Column 6, line 6, change "zero-crosslinked" to --non-crosslinked--

Column 6, line 10, change "capillaries" to --capillary--

Column 6, line 48, change "M13mp18DNA" to --M13mp18 DNA--

Column 7, line 16, change "9T" to --9% T--

Column 7, line 17, change "run" to --performed--

Column 7, line 27, after "DNA" insert --sequencing--

Column 7, line 67, change "NvT/2D" to --N=vT/2D--

Column 8, line 2, change "easily seen" to --easily detected--

Column 8, line 8, after "reliable" insert --scan--

UNITED STATES PATENT AND TRADEMARK OFFICE
CERTIFICATE OF CORRECTION

PATENT NO. : 5,274,240

DATED : December 28, 1993

INVENTOR(S) : Richard A. Mathies et al.

It is certified that error appears in the above-identified patent and that said Letters Patent is hereby corrected as shown below:

Column 8, line 19, change "lane-to-lane" to --capillary-to-capillary--

Column 8, line 25, change "lane-to-lane" to --capillary-to-capillary--

Column 8, line 50, change "540 m" to --540 nm--

Column 8, line 55, change "610 m" to --610 nm--

Column 9, line 39, change "derivations" to --derivitization--

Columns 9 and 10, number references 1-28

Column 10, reference no. 24, change "Rye, J.S.;" to --Rye, H.S.;--

Column 10, reference no. 27, after "J. Chromatogr." insert --1991--

Column 12, line 41, after "collect said" delete --the--

Column 13, line 6, change "is" to --are--

Signed and Sealed this

Eleventh Day of October, 1994

Attest:

BRUCE LEHMAN

Attesting Officer    Commissioner of Patents and Trademarks